United States Patent [19]

Nathan

[11] 4,090,504
[45] May 23, 1978

[54] PORTABLE TEMPERATURE AND PULSE MONITOR

[76] Inventor: Yehuda Nathan, 1717 50th St., Brooklyn, N.Y. 11204

[21] Appl. No.: 697,851

[22] Filed: Jun. 21, 1976

[51] Int. Cl.² .............................................. A61B 5/02
[52] U.S. Cl. .......................... 128/2.05 R; 128/2.05 T; 128/2 H; 128/DIG. 15
[58] Field of Search ...................... 128/2.05 P, 2.05 R, 128/2.05 S, 2.05 T, 2 H, 2.06 E, 2.06 F, DIG. 29

[56] References Cited

U.S. PATENT DOCUMENTS

| 3,530,851 | 9/1970 | Geschickter | 128/2.06 E |
| 3,534,727 | 10/1970 | Roman | 128/2.06 E |
| 3,572,316 | 3/1971 | Vogelman et al. | 128/2.05 R |
| 3,792,700 | 2/1974 | Sarnoff et al. | 128/2.06 E X |
| 3,802,698 | 4/1974 | Burian et al. | 128/2.05 P |
| 3,807,388 | 4/1974 | Orr et al. | 128/2.05 R X |
| 3,871,362 | 3/1975 | Dunegan | 128/2 H X |
| 3,884,219 | 5/1975 | Richardson et al. | 128/2 R |
| 3,916,877 | 11/1975 | Beckman | 128/2 H X |
| 3,940,742 | 2/1976 | Hudspeth et al. | 340/172.5 |
| 3,978,849 | 9/1976 | Geneeu | 128/2.05 T X |
| 4,005,701 | 2/1977 | Aisenberg et al. | 128/2.05 S X |

OTHER PUBLICATIONS

"Recording Infant Heart Rate Patterns in the Home" Spurlock, J. M. et al., Journal of Assoc. for Advancement of Medical Instrumentation vol. 5, No. 5, Sept.-Oct. 1971, pp. 290-296.

*Physical Diagnosis,* Hochstein & Rubin, McGraw-Hill, N.Y. 1964 pp. 27-28.

"A Cardiotachometer which calculates Rate Digitally", by Elings & Holly IEEE Transactions on Biomedical Engineering, Nov. 1973.

*Primary Examiner*—Robert W. Michell
*Assistant Examiner*—Francis J. Jaworski
*Attorney, Agent, or Firm*—Natter & Natter

[57] ABSTRACT

A medical diagnostic and monitoring apparatus for electronically measuring a patient's internal body temperature and pulse frequency. An electrothermic transducer and an electroacoustic transducer are placed within a yieldable mounting pad attached to a flexible shoulder strap and provide a signal sending unit. The sending unit is adapted for placement in an underarm axillary space for temperature detection and pulse sensing. A portable display console includes a power source for actuating output signals from the sending unit and includes digital logic circuitry for processing and converting the signals for readout on a visual numeric display.

10 Claims, 6 Drawing Figures

U. S. Patent  May 23, 1978  Sheet 2 of 2  4,090,504
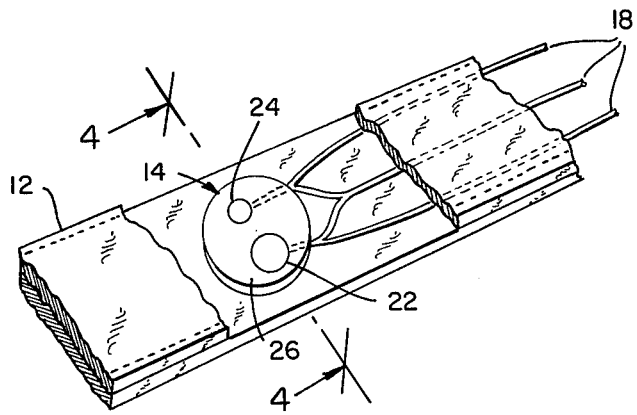
FIG. 3
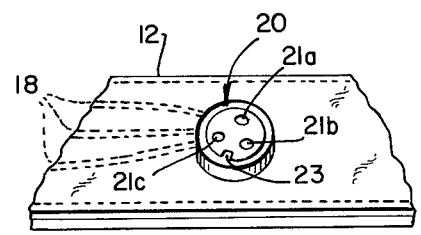
FIG. 5
FIG. 4
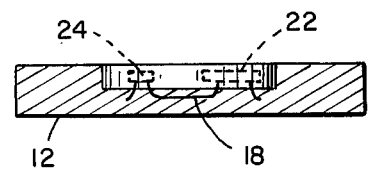
FIG. 6
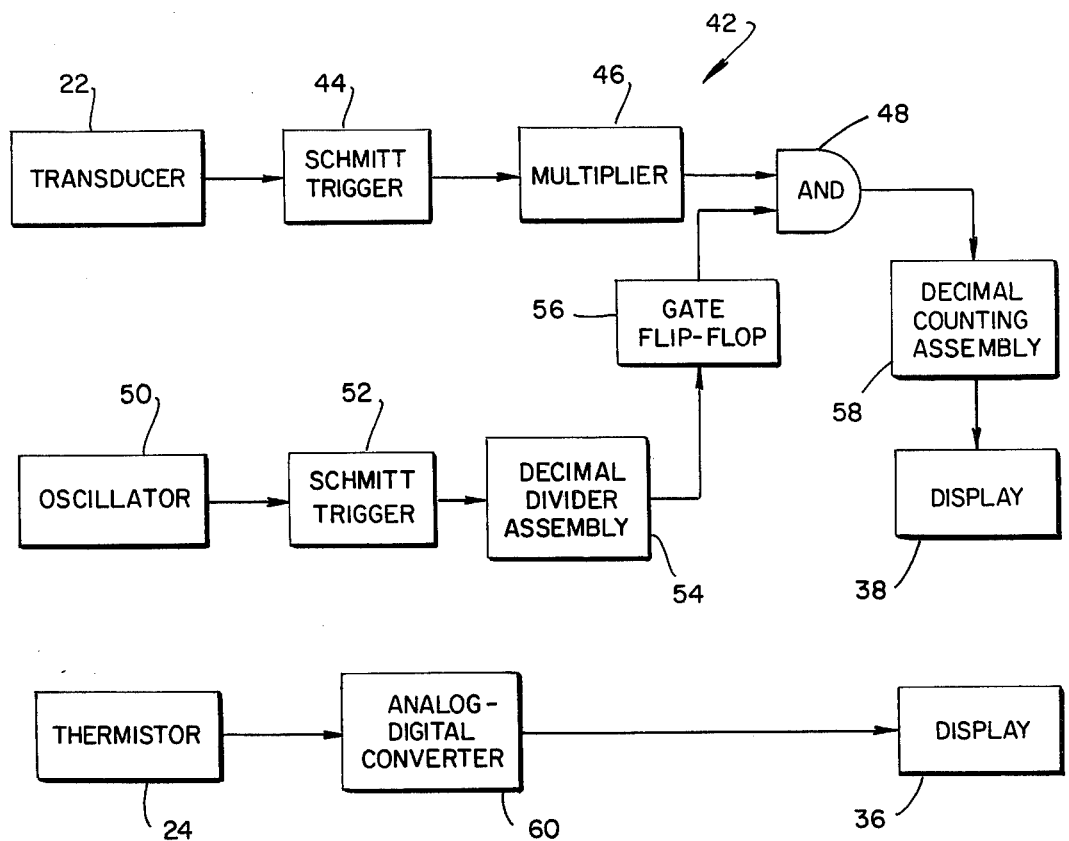

PORTABLE TEMPERATURE AND PULSE MONITOR

BACKGROUND OF THE INVENTION

1. Field of the Invention

The invention relates generally to medical apparatus and especially to a diagnostic and monitoring device for electronically measuring body temperature and pulse frequency.

The patient monitoring system of this invention utilizes a temperature responsive component, such as an electrothermic transducer for detecting internal body temperature and an electroacoustic transducer for sensing pulse rate or frequency.

2. Description of the Prior Art

Currently used electronic patient monitoring systems are commonly employed in intensive care quarters and coronary care units. The equipment used frequently includes one or more pieces of bedside apparatus hard-wired to a central monitoring position which is manned by a nurse or otherwise provided with an alarm signal. Similar types of equipment are also applied in operating room systems. The aforementioned medical apparatus is generally adapted for the simultaneous monitoring of several different body functions, and the patient must be fitted with numerous probes, electrodes, hypodermic needles and other sensing devices, the attachment of which to the patient can be cumbersome, time consuming and may require the services of a nurse or trained technician. Furthermore, the circumstances under which this equipment is used are usually in critical situations and concern about patient disturbance or discomfort would not be a prime consideration. Additionally, this medical equipment is rather expensive and consequently is not available for hospital patients outside of the special care units as above noted.

Another system for monitoring the temperature of a patient employs a radio frequency communication link between a transmitter carried by the patient and is discussed in U.S. Pat. No. 3,921,621. A problem with this last mentioned system is that it would be subject to radio interference which is generated by hospital equipment.

The apparatus of this invention is designed for the detention and measuring of pulse rate and internal body temperature under ordinary circumstances within or outside of the hospital.

The pule rate is conventionally counted at locations where an artery approaches the surface of the body. Such locations in the upper extremity or limb anatomically occur at the radial artery in the wrist and at the brachial artery along the inner or medial side of the arm near the biceps. The instant invention in contrast detects blood pressure change in the arterial circulation system at a main trunk located in close proximity to the heart. Accordingly, the alternate expansion and contraction of the artery which constitutes the pulse is measured as this pressure change is brought about by ejection of blood from the heart into the aorta and propagates as a wave through the blood column. The blood flows through a conduit or tubular channel constituting the aorta and into a subclavian artery through the axillary artery and into the brachial artery during its flow down the arm and toward the hand. By positioning a pulse sensing unit within the axillary space or fossa formed between the medial or inner side of the arm and the lateral surface of the chest wall commonly referred to as the underarm region, an electroacoustic transducer can sense the blood flow through the axillary artery. Since a fascia or band of connective tissue invests or envelops the axillary artery in a sheath which includes other large vessels and nerves, it has been found that by positioning the transducer at the apex of this pyramidal compartment or axillary space the closest proximity to the axillary artery can be reached. Furthermore, the adipose or fatty padding tissue in the fossa will surround the temperature responsive element and thus provide a reliable indication of the internal body temperature. It should thus be apparent that by positioning both the pulse detecting and temperature responsive components at the apex of the axillary space both of these physiological variables can be determined. A feature of this invention is the recognition and utilization of the fossa or depression forming the armpit as a desirable anatomic location for positioning of such instrument.

A further feature of this invention is that the transducer is mounted in a disposable flexible cloth shoulder strap which can be positioned on the patient upon entering the hospital and remain with the patient during his stay. A nurse or attendant carrying a hand-held display console can quickly and effectively determine the temperature and pulse rate of each patient by interconnecting a removable plug with a mating receptacle on the shoulder strap. Within about fifteen seconds a determination can be made as to these temperature and pulse rate values and the patient need not be moved or disturbed while obtaining such readings.

BRIEF DESCRIPTION OF THE INVENTION

The subject matter of this invention is directed to a patient monitoring system and apparatus for electronically measuring internal body temperature and pulse frequency. A temperature responsive electrothermic transducer and a sound responsive electroacoustic transducer are placed within a yieldable mounting pad attached to a flexible cloth shoulder strap and provide a signal sending unit. The strap is adapted for circumscribable attachment over the patient's shoulder with the sending unit being positioned for underarm placement at the apex of the axillary space.

A portable display console having a self-contained DC power source is selectively interconnectible to the sending unit which in turn generates output signals corresponding to a patient's physiologial variables of heart beat and internal body temperature. These signals are processed through appropriate signal conditioners for amplifying, refining and selecting certain portions for interpolation through the application of digital logic instrumentation so as to provide a visual numeric display.

The purpose of the invention is to provide an apparatus for permitting a nurse or hospital attendant to readily determine the body temperature and pulse rate of a patient without disturbing or otherwise inconveniencing the patient.

An important aspect of this invention is the proper placement of the sending unit in contact with the patient's body. It has been found that the critical region or axillary space under the arm and within the armpit area provides for relatively accurate and representative readings of the patient's temperature. Additonally, this area adjacent to the chest cavity and heart contains large arteries such as the axillary artery; thus an electroacoustic transducer or microphone will respond to the rhythmic sounds produced by the heart or by the flow of blood through the arteries. An alternate component such as a pressure sensitive transducer resting against the surface of the body tissue adjacent the artery can also be used to detect the rhythmic flow of blood which can be translated to the pulse beat.

A feature of this invention is the utilization of a shoulder strap which incorporates a cushion or yieldable pad for mounting the transducers. The shoulder strap is adapted for placement on the patient circumscribing the shoulder for positioning the sending unit at a desired location.

In operation, the power source is contained within a visual display console which can be interconnected to the shoulder strap at a convenient location having a female socket or receptacle, and a readout can be obtained.

Having thus summarized the invention, it will be seen that an object thereof is to provide a medical diagnostic and monitoring apparatus of the general character described herein which is not subject to the disadvantage of the prior art.

Specifically, it is an object of the instant invention to provide a medical diagnostic apparatus for monitoring body temperature and pulse rate.

It is a further object of this invention to provide a medical diagnostic apparatus including a shoulder strap for positioning the detection and transmission components against the patient's body in an area under the arm.

Another object of this invention is to provide a companion portable display unit for use in conjunction with the power source for actuating the sending unit to obtain a readout.

The above and other objects, features and advantages of this invention will be readily apparent from the following description of the preferred embodiment, when considered in conjunction with the accompanying drawings.

BRIEF DESCRIPTION OF THE DRAWINGS

In the appended drawings in which are shown the preferred embodiments of the invention:

FIG. 3 is a perspective view of a portion of the shuolder strap shown to an enlarged scale with a portion being cut away to expose the cushion pad for mounting an electrothermic transducer and an electroacoustic transducer;

FIG. 4 is an enlarged sectional view taken substantially along line 4—4 of FIG. 3 and shows the mounting of the transducer semiconductive components within the foam cushion pad for placement against the skin surface;

FIG. 5 is a perspective view of a portion of the shoulder strap showing the socket portion incorporated therein for receiving a connective plug from the display unit; and FIG. 6 is a functional block diagram illustrating operation of the apparatus.

DETAILED DESCRIPTION OF THE INVENTION

Figure 1:
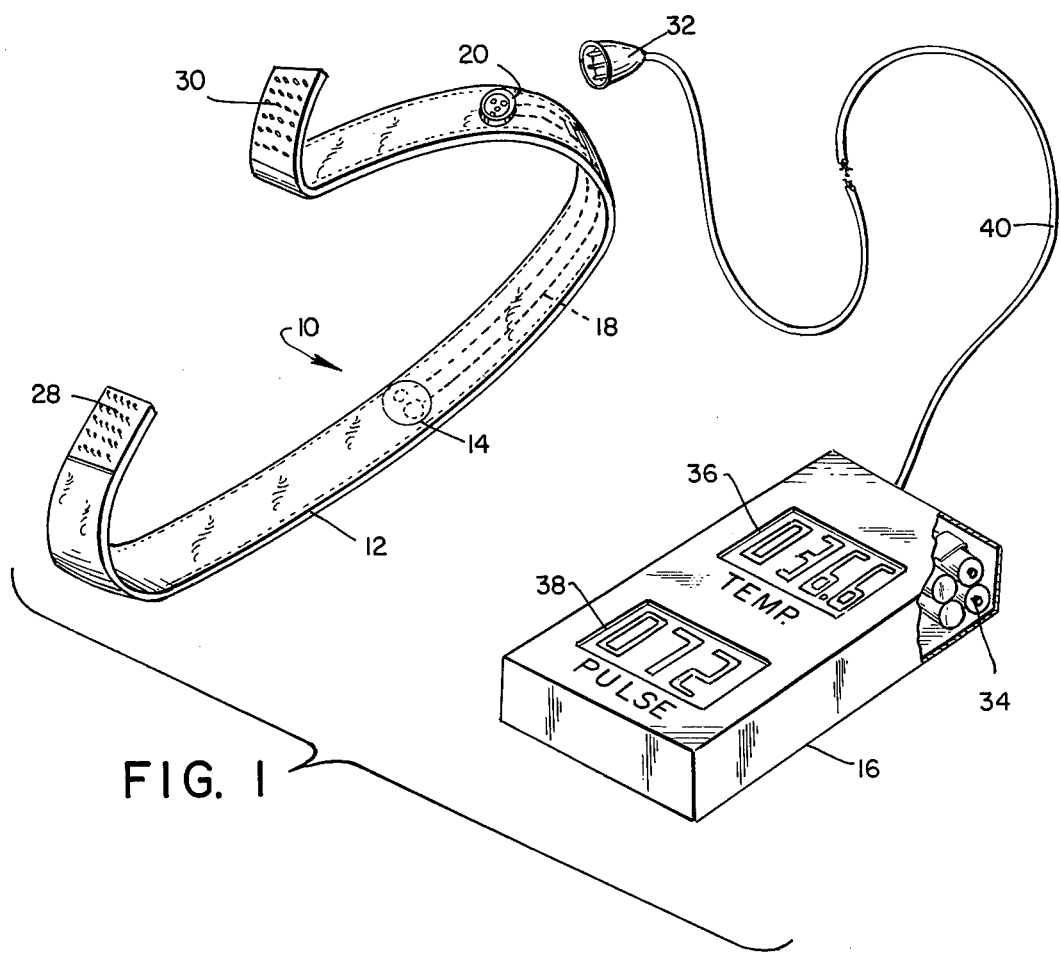
FIG. 1 is a perspective view of the medical diagnostic apparatus of this invention showing the shoulder strap and visual display unit.

Referring now in detail to the drawings, the reference numeral 10 refers generally to a diagnostic medical apparatus of this invention. The medical apparatus 10 includes a shoulder strap 12 supporting a body function monitoring and sending unit 14 for use in conjunction with a portable console 16 containing a DC power source and digital logic circuitry for producing a visual numeric readout.

The shoulder strap 12 is preferably fabricated from a flexible cloth material and has an integral wiring system 18 incorporated therein for conductively interconnecting the monitoring and sending unit to a receptacle 20.

The sending unit 14 is comprised of an electroacoustic transducer such as microphone 22 and an electrothermic transducer such as a solid state semiconducting device or thermistor 24. It should be apparent that other equivalent sensing devices can be used to accomplish the same functions as specified herein. Further, a pressure transducer can be substituted for the electroacoustic transducer. The transducers 22 and 24 are adapted to be pocketed within a yieldable mounting such as a foam cushion or pad 26 as noted in FIGS. 3 and 4. This recessed shock mounting arrangement will not only protect the transduers 22, 24, but will also fixedly position them on the inner face of the strap 12 for operative placement on a patient's body. The yieldable mounting pad 26 provides comfortable yet close contact with the body surface of the patient. The free ends of the strap 12 are provided with adjustable fastener devices such as mating hooks 28 and eyes 30 commercially available under the trademark Velcro. The receptcle 20, as shown in FIGS. 1 and 5, is mounted on an external face of the shoulder strap 12 and has a grouping of receiving apertures 21a, 21b, 21c which are keyed by a channel 23 to insure correct alignment for accommodating a three-pin connector plug 32.

The shoulder strap 12 is adapted to be placed on the patient upon entering the hospital and to remain with the patient for the duration of the stay. Further, since the shoulder strap 12 can be fabricated of relatively inexpensive material and the solid state sending unit 14 can be economically replaced, the unit 14 including strap 12 can be designed for disposable use. This will avoid the necessity of cleaning and/or sterilization before issuing same to a new patient.

Figure 2:
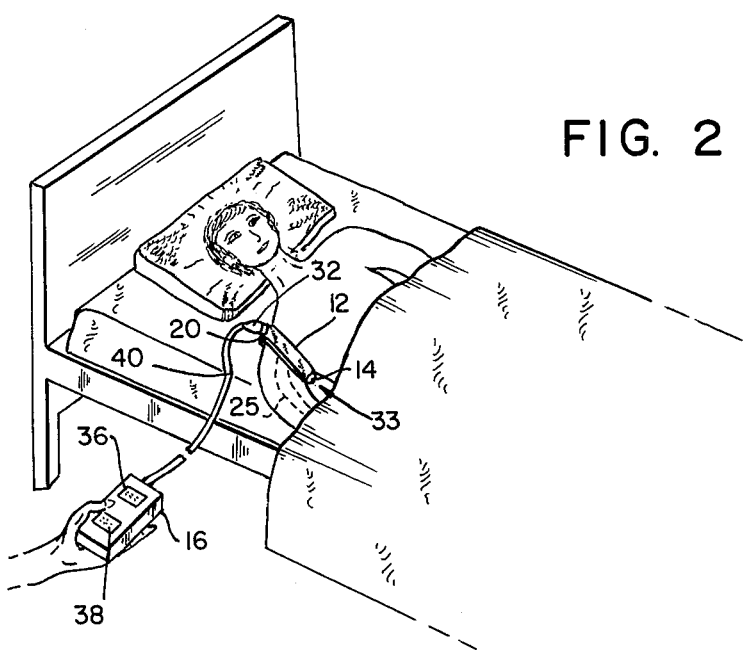
FIG. 2 is a pictorial representation illustrating a typical application of the present invention.

An important aspect of the device is the ability to obtain accurate and reliable readings of both pulse beat and body temperature in a relatively short time of approximately 15-20 seconds. For this purpose, it has been found that the sending unit 14 should be held in a critical underarm area 33, being anatomically defined as the apex of the axillary space. The shoulder strap 12 is shown so affixed to a patient in FIG. 2. The electrothermic transducer 24 will accurately respond to body temperature by changing its electrical resistance, which varies with the temperature. This change can be monitored by digital logic instrumentation and calibrated in degrees, preferably within the range of 32°-46° C. Furthermore, the electroacoustic transducer 22 will be in close proximity to an axillary artery 25 when so positioned and can thus respond to the rhythmic sound of the alternate expansion and contraction of the artery to generate corresponding pulses.

The portable display console 16 is provided with a power source such as a battery pack 34 and has a temperature display 36 and a pulse frequency display 38. A flexible electric connection 40 extends from the console 16 and terminates at the three-pin connector plug 32. The plug 32 is adaptable for accommodation within the receptacle 20 noted in FIG. 5. An integrated digital logic circuit 42 shown in FIG. 6 is within console 16 and electronically processes the pulse input signals.

The block diagram of FIG. 6 illustrates the pulse rate determination which is detected by the electroacoustic transducer 22. The output signal from the transducer 22 in the form of an electric pulse is processed to adjust the pulse amplitude to a value that operates a bistable multivibrator or Schmitt trigger 44 and converts the signals to square wave pulses. The pulses are then fed to a multiplier 46 to increase the pulse frequency. Typically, the signal frequency is increased fourfold and the input signal fed to an upper AND gate 48. To gate the lower AND input circuit a stable crystal (clock) oscillator 50 such as a quartz crystal is used, and the clock signals are fed through another Schmitt trigger 52 to produce constant amplitude square wave pulses which are fed to a decimal divider assembly 54 to produce a desired interval such as 15 second output. This output signal operates a gate flip-flop 56 that opens the AND gate 48 for this precise period of time and then closes it. During this interval the upper input is enabled and each pulse into the upper input of the gate is counted by a decimal counting assembly 58 for numeric readout on the visual display 38. At the end of the time interval the display remains momentarily until the next interval flip-flop is activated. It is possible to inhibit the gate flip-flop to make the display on the decimal counting assembly 58 as long as desired.

The temperature measuring circuit processes input signals from the electrothermic transducer 24, e.g., a thermistor, having a temperature responsive element which has a negative coefficient of resistance. The resistance decreases with increasing temperature to provide corresponding voltage differential. This change in resistance can be accurately measured and displayed as discrete numerals with a digital voltmeter or multimeter similar to a Weston Model 1240 meter and can be calibrated for readout in degrees of temperature.

For the sake of simplicity, the circuit shown includes an analog to digital converter 60 using known conversion techniques and having a numeric readout on the display 36. It should be apparent that the apparatus 10, when used in conjunction with console 16, will provide a rapid and accurate system for determining pulse rate frequency and internal body temperature.

The above cited embodiment is intended an exemplary, and while it has described the invention with specific implementation thereof, other modifications and changes might be made in this embodiment as set forth and will be understood that all material shown and described in the accompanying drawings is to be interprted as illustrative and not in a limiting sense, and the invention should be considered as comprehensive of all of the same which come within the scope of the appended claims.

Having thus described the invention, there is claimed as new and desired to be protected by Letters Patent:

1. A medical diagnostic and monitoring apparatus for electronically measuring a patient's internal body temperature and pulse frequency comprising at least two sensing components for respectively detecting a patient's physiological variables of temperature and pulse rate, support means for retaining said sensing components under the patient's arm, the support means including a strap, said strap being adapted to circumscribe the patient's shoulder, yieldable mounting means on said strap for accommodating said sensing components, fastening means for adjustably securing the strap to the patient with the sensing components being anatomically positioned in continuous contact with the patient's body at the apex of the axially space, said contact within the axillary space providing a source of input data detectable by the sensing components, said support means further including a receptacle mounted on said strap and conductively interconnected to said sensing components, a companion display unit, said display unit being selectively connectible to the receptacle for actuating the sensing components to transmit electrical signals corresponding to said physiological variables, and digital logic circuitry within said display unit for processing said signals to provide a visual numeric display.

2. A medical dignostic and monitoring apparatus as claimed in claim 1 wherein the sensing components comprise an electroacoustic transducer for responding to pulse pressure change and an electrothermic transducer for responding to temperature variation.

3. A medical diagnostic and monitoring apparatus as claimed in claim 1 wherein the temperature sensing component comprises a thermistor for detecting body temperature at the apex of the axillary space, and further including means for measuring resistance and converting same to be corresponding visual numeric readout in degrees of temperature.

4. A medical diagnostic and monitoring apparatus as claimed in claim 3 wherein the output from the thermistor is processed through an analog to digital converter.

5. A medical diagnostic and monitoring system as claimed in claim 1 wherein the pulse rate detection sensing component comprises an electro-acoustic transducer and further including bistable multivibrator means for converting an input signal to a square wave pulse, oscillator means for generating fixed frequency pulses, gating means actuated by said fixed frequency pulses for determining selected period measurments of the square wave pulses and decimal counting assembly means for counting and displaying the square wave pulses counted during the selected period.

6. A medical diagnostic and monitoring apparatus as claimed in claim 5 wherein the sensing component comprises a microphone and the bistable multivibrator means includes a Schmitt trigger.

7. A medical diagnostic and monitoring apparatus as claimed in claim 5 wherein the oscillator means comprises a stable quartz crystal adapted to provide fixed frequency clock signals.

8. A medical diagnostic and monitoring apparatus as claimed in claim 1 wherein the yieldable mounting means includes a cushion pad formed on an interior face of the strap, said pad defining recessed pockets for receiving the respective sensing components to provide comfortable patient contact during operative placement of the strap.

9. A medical diagnostic and monitoring apparatus as claimed in claim 1 wherein the display unit has a self-contained power source and is adapted for conductive interconnection with the receptacle and the support means being suitable for disposable patient use.

10. A portable temperature and pulse monitor for measuring a patient's internal body temperature and pulse rate comprising disposable shoulder strap means adapted for adjustable securement encircling a patient's shoulder and underarm, said strap means having sensing means for detecting the patient's temperature and pulse rate, yieldable mounting means within said strap means for accommodating the sensing means and positioning same in cushioned contact with the patient's body within the axillary space, said strap means further including integral wiring extending from the sensing means and terminating at a receptacle on an external face of the strap, a hand-held portable console means having a self-contained power source, said console means having a connector plug for selective interconnection to the receptacle for receiving and processing input signals from the sensing means and for converting same to a visual display corresponding to the physiological variables being monitored.

* * * * *